(12) United States Patent
Yun et al.

(10) Patent No.: US 10,426,950 B2
(45) Date of Patent: Oct. 1, 2019

(54) METHODS AND DEVICES FOR TREATING PARASYMPATHETIC BIAS MEDIATED CONDITIONS

(71) Applicant: Palo Alto Investors, Palo Alto, CA (US)

(72) Inventors: Anthony Joonkyoo Yun, Menlo Park, CA (US); Jeremy Thomas Yun, Menlo Park, CA (US); Eric Foster Yun, Menlo Park, CA (US)

(73) Assignee: Palo Alto Investors, Palo Alto, CA (US)

(*) Notice: Subject to any disclaimer, the term of this patent is extended or adjusted under 35 U.S.C. 154(b) by 0 days.

(21) Appl. No.: 14/012,771

(22) Filed: Aug. 28, 2013

(65) Prior Publication Data

US 2014/0065129 A1 Mar. 6, 2014

Related U.S. Application Data

(60) Provisional application No. 61/772,403, filed on Mar. 4, 2013, provisional application No. 61/762,223, filed on Feb. 7, 2013, provisional application No. 61/694,630, filed on Aug. 29, 2012.

(51) Int. Cl.
*A61N 1/05* (2006.01)
*A61K 45/00* (2006.01)
*A61N 1/36* (2006.01)

(52) U.S. Cl.
CPC ........... *A61N 1/0551* (2013.01); *A61K 45/00* (2013.01); *A61N 1/3605* (2013.01); *A61N 1/3606* (2013.01); *A61N 1/36014* (2013.01); *A61N 1/36017* (2013.01); *A61N 1/36085* (2013.01); *A61N 1/36167* (2013.01)

(58) Field of Classification Search
CPC ........... A61N 1/36014; A61N 1/36017; A61N 1/3605; A61N 1/3606; A61N 1/0551; A61N 1/36085; A61N 1/36167; A61K 45/00
See application file for complete search history.

(56) References Cited

U.S. PATENT DOCUMENTS

| | | | |
|---|---|---|---|
| 7,149,574 B2 | 12/2006 | Yun et al. | |
| 7,363,076 B2 | 4/2008 | Yun et al. | |
| 7,711,430 B2* | 5/2010 | Errico | A61N 1/36114 607/42 |
| 7,738,952 B2 | 6/2010 | Yun et al. | |
| 7,899,527 B2 | 3/2011 | Yun et al. | |
| 8,569,277 B2 | 10/2013 | Yun et al. | |
| 8,571,650 B2 | 10/2013 | Yun | |
| 2004/0249416 A1 | 12/2004 | Yun et al. | |
| 2005/0021092 A1 | 1/2005 | Yun et al. | |
| 2005/0143378 A1 | 6/2005 | Yun et al. | |
| 2005/0143788 A1 | 6/2005 | Yun et al. | |
| 2005/0153885 A1 | 7/2005 | Yun et al. | |
| 2005/0240241 A1 | 10/2005 | Yun et al. | |
| 2005/0256028 A1 | 11/2005 | Yun et al. | |
| 2006/0116721 A1* | 6/2006 | Yun et al. | 607/2 |
| 2010/0119482 A1 | 5/2010 | Yun et al. | |
| 2010/0144691 A1 | 6/2010 | Yun et al. | |
| 2010/0260669 A1 | 10/2010 | Yun et al. | |
| 2010/0286734 A1 | 11/2010 | Yun et al. | |
| 2012/0270876 A1 | 10/2012 | Yun et al. | |
| 2013/0053817 A1 | 2/2013 | Yun | |

OTHER PUBLICATIONS

Belza et al. (2005). Bioactive food stimulants of sympathetic activity: effect on 24-h energy expenditure and fat oxidation. Eur J Clin Nutr, v59(6), p. 733-741.*
Basso et al. (2003). Neural correlates of IgE-mediated food allergy. Journal of Neuroimmunology, v140, p. 69-77.*
Liang et al. (2011). Vagal activities are involved in antigen-specific immune inflammation in the intestine. Journal of Gastroenterology and Hepatology, v26(6), p. 1065-1071.*
Bray (2000). Reciprocal relation of food intake and sympathetic activity: experimental observations and clinical implicationsInternational Journal of Obesity, v24 (Suppl 2), S8-S17.*
Lenard et al. (2008). Central and Peripheral Regulation of Food Intake and Physical Activity: Pathways and Genes. Obesity, v16(Suppl 3), S11-S22.*
"About food allergies, treating and managing reactions" Retrieved from http://www.foodallergy.org/treating-an-allergic-reaction.*
Adrenaline (epinephrine). (2006). In Churchill Livingstone's dictionary of nursing. Philadelphia, PA: Elsevier Health Sciences. Retrieved from http://search.credoreference.com/content/entry/ehscldictnursing/adrenaline_epinephrine/0.*
Grassi et al. (2008). Essential hypertension and the sympathetic nervous system. Neurol. Sci., v29, S33-S36.*
Vesalainen et al. (1998). Vagal Cardiac Activity in Essential Hypertension: The Effects of Metoprolol and Ramipril. American Journal of Hypertension, v11, p. 649-658.*
McClain et al. (2006). Animal Models of Food Allergy: Opportunities and Barriers. Current Allergy and Asthma Reports; v6, p. 141-144.*
Miller et al. Depressed children with asthma evidence increased airway resistance: "Vagal bias" as a mechanism. J Allergy Clin Immunol (2009), v121(1), p. 66-73 and 73.e1-73.e10.*
Ruiter et al. Permanent cardiac pacing for neurocardiogenic syncope. Netherlands Heart Journal (2008), v16(Suppl. 1), p. 15-19.*
Bradycardia. (2005). In R. Youngson, Collins Dictionary of medicine. London, UK: Collins. Retrieved from http://search.credoreference.com/content/entry/collinsmed/bradycardia/0.*
Artificial Pacemaker (2008). Internet article, 1 page.*
Aydin et al. Management and therapy of vasovagal syncope: A review. World Journal of Cardiology (2010), v2(10), p. 308-315.*
Sicherer et al. Food allergy. J Allergy Clin Immunol (2010), v125, S116-25.*
Bock et al. Fatalities due to anaphylactic reactions to foods. J Allergy Clin Immunol (2001), v107, p. 191-193.*
Anaphylaxis (2011). Internet Article, 3 pages.*

(Continued)

*Primary Examiner* — Sean C. Barron
(74) *Attorney, Agent, or Firm* — Otto C. Guedelhoefer, IV; Bret E. Field; Bozicevic, Field & Francis LLP

(57) ABSTRACT

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

21 Claims, No Drawings

(56) References Cited

OTHER PUBLICATIONS

Fiocchi et al. World Allergy Organization (WAO) Diagnosis and Rationale for Action against Cow's Milk Allergy (DRACMA) Guidelines. Pediatr Allergy Immunol (2010), v21(Suppl. 21), p. 1-125.*

Simons et al. EpiPen Jr versus EpiPen in young children weighing 15 to 30 kg at risk for anaphylaxis. J Allergy Clin Immunol (2002), v109, p. 171-175.*

Fleming et al. Normal ranges of heart rate and respiratory rate in children from birth to 18 years of age: a systematic review of observational studies. The Lancet (2011), v377, p. 1011-1018.*

Fukutomi et al. Abnormal responses of the autonomic nervous system in food-dependent exercise-induced anaphylaxis. Annals of Allergy (1992), v68, p. 438-445. (Year: 1992).*

Jardine et al. Autonomic control of vasovagal syncope. Am J Physiol (1998), v274 (6 Pt 2), H2110-2115. (Year: 1998).*

Permaul et al. Anaphylaxis in a Patient with Long QT Syndrome. J. Allergy Clin Immunol (2007), Abstract 132. (Year: 2007).*

"Heart Rate Variability Monitor for Patient Assessment and Treatment". Internet Article by BioCom Technologies, 1 page. (Year: 2009).*

Yokusoglu et al. Heart Rate Variability in Patients with Allergic Rhinitis. Military Medicine (2007), v172, p. 98-101). (Year: 2007).*

De Luca et al. [A correlation between food allergy, the autonomic nervous system and the central nervous system: a study of 8 patients in childhood]. Pediatr. Med. Chir. (1996), v18(6), p. 565-571, Abstract only. (Year: 1996).*

* cited by examiner

METHODS AND DEVICES FOR TREATING PARASYMPATHETIC BIAS MEDIATED CONDITIONS

CROSS REFERENCE TO RELATED APPLICATIONS

Pursuant to 35 U.S.C. § 119 (e), this application claims priority to the filing date of U.S. Provisional Application Ser. No. 61/772,403 filed on Mar. 4, 2013; U.S. Provisional Application Ser. No. 61/694,630 filed on Aug. 29, 2012 and U.S. Provisional Application Ser. No. 61/762,223 filed Feb. 7, 2013; the disclosures of which applications are herein incorporated by reference.

INTRODUCTION

There are a variety of conditions that can affect an individual's health and well-being. The treatment of various conditions that affect the health and well-being of an individual has been around for centuries. Such treatments include pharmacological, surgical, and life style (dietetic, exercise, etc.) changes. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative of the disorder itself. In fact, treatment protocols effectively directed at the underlying cause of a condition are quite rare.

As such, there continues to be an interest in the development of new protocol options for treating conditions. Of particular interest are protocols for treating conditions that are directed at the cause of the condition rather than the symptoms thereof.

SUMMARY

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

DETAILED DESCRIPTION

Methods for treating a subject for a parasympathetic bias mediated condition are provided. Aspects of the methods include modulating at least a portion of the subject's autonomic nervous system to increase the sympathetic/parasympathetic activity ratio in a manner effective to treat the subject for the parasympathetic bias mediated condition. In some instances, the subject is known to have parasympathetic bias. Also provided are devices that find use in practicing various embodiments of the methods.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the invention, aspects of embodiments of methods of the invention are described first in greater detail, followed by a review of examples of applications in which the subject methods find use, as well as a description of representative devices which find use in practicing various embodiments of the methods.

Methods

Parasympathetic Bias Mediated Conditions

As summarized above, aspects of the invention include methods of treating a subject for a parasympathetic bias mediated condition. Parasympathetic bias mediated conditions are physiological conditions having one or more undesirable symptoms, where the symptoms arise (at least in part) from parasympathetic bias (at least in a portion of the subject's autonomic nervous system). Parasympathetic bias mediated conditions include both chronic and acute conditions. In some instances, the conditions of interest are disease conditions. In some instances, the conditions of interest are conditions arising in response to one or more stimuli, e.g., ingestion of nutritional or therapeutic compositions, exposure to certain environmental conditions, infection with a pathogenic agent, induction of stress, e.g., from exercise, etc. Examples of specific conditions of interest are provided in greater detail below.

Autonomic Function Modulation

Aspects of methods of the invention include treating a subject for a parasympathetic bias mediated condition by modulating autonomic function in the subject. By "modulating" is meant altering or changing one aspect or component to provide a change, alteration or shift in another aspect or component. Modulating autonomic function is achieved by modulating at least one portion of the subject's autonomic nervous system. By "modulating at least one portion of the subject's autonomic nervous system" is meant altering or changing at least a portion of an autonomic nervous system by a means to provide a change, alteration or shift in at least one component or aspect of the autonomic nervous system.

Methods of modulating at least one portion of the subject's autonomic nervous system according to certain embodiments include modulating the parasympathetic and/or sympathetic activity in the subject. "Parasympathetic activity" refers to activity of the parasympathetic nervous system whereas "sympathetic activity" refers to activity of the sympathetic nervous system. Also, as used herein, "activity" and "function" are used interchangeably. In some embodiments, methods include at least one of decreasing parasympathetic activity and or increasing sympathetic activity in a subject.

A subject's autonomic nervous system may be modulated using any convenient protocol, including electrical and/or pharmacologic protocols. As such, embodiments of the subject methods include modulating at least one portion of the subject's autonomic nervous system to treat a subject for a target condition by administering an effective amount of a pharmacological agent and/or applying an appropriate electrical stimulation to the subject. Pharmacologically modulating at least a portion of a subject's autonomic nervous system is also herein referred to as modulating the autonomic nervous system by utilizing a "pharmacological protocol". Electrically modulating at least a portion of a subject's autonomic nervous system is also herein referred to as modulating the autonomic nervous system by utilizing an "electrical protocol". The pharmacological and/or electrical modulation may provide an increase in function of at least a portion of the autonomic system, e.g., increase function in at least one sympathetic nerve fiber, and/or provide a decrease in function or dampening of a portion of the autonomic system, e.g., may inhibit activity in at least one parasympathetic nerve fiber or inhibit nerve pulse transmission.

The pharmacological and/or electrical modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ, e.g., lung, or even to a particular nerve fiber. For example, localization may be with respect to innervations of one or more organs. Area(s) of the autonomic nervous system may include, but are not limited to, preganglionic and postganglionic nerve fibers, ganglionic structures, efferent and afferent nerve fibers, the hypothalamus, receptors on the hypothalamus, afferent autonomic nerves (sympathetic and parasympathetic) and hormonal receptors on the hypothalamus. In certain embodiments, a given nerve fiber or the like may be modulated with respect to sympathetic and/or parasympathetic activity in more than one area of the nerve fiber.

In some instances, the modulation that is achieved in practicing methods of the invention may be quantified. One way of quantifying modulation of at least one portion of the subject's autonomic nervous system is the parasympathetic/sympathetic activity ratio. By "parasympathetic/sympathetic activity ratio" is meant the ratio of activity of the sympathetic nervous system to the activity of the parasympathetic nervous system. As such, methods according to certain embodiments include modulating a sympathetic/parasympathetic activity ratio in the subject.

In some instances, at least a portion of the autonomic nervous system may be modulated to alter, shift or change parasympathetic activity and/or sympathetic activity from a first state to a second state, where the second state is characterized by a increase in the sympathetic activity/parasympathetic activity ratio relative to the first state. Accordingly, embodiments of the subject invention include modulating at least a portion of a subject's autonomic nervous system to increase the sympathetic activity/parasympathetic activity ratio, i.e., to increase sympathetic activity relative to parasympathetic activity (in other words to decrease parasympathetic activity relative to sympathetic activity) so as to treat a subject for a food allergy syndrome condition. Increasing the sympathetic activity/parasympathetic activity ratio may be achieved by stimulating the sympathetic system to increase activity in at least a portion of the sympathetic system, e.g., stimulating at least one sympathetic nerve fiber. Alternatively or in addition to stimulating at least one sympathetic nerve fiber to increase activity, increasing the sympathetic activity/parasympathetic activity ratio may be achieved by inhibiting activity in the parasympathetic system, e.g., inhibiting activity in at least one parasympathetic nerve fiber to achieve an increased sympathetic activity relative to parasympathetic activity. Still further, in certain embodiments the subject invention provides methods of both increasing activity in at least one sympathetic nerve fiber and inhibiting activity in at least one parasympathetic nerve fiber to achieve the desired result.

As will be described in greater detail below, while the ratio of sympathetic function/parasympathetic function may be increased according to embodiments of the subject invention to treat a subject for a condition, such as a food allergy syndrome condition, the net result may be a sympathetic bias (i.e., sympathetic dominance), or the activities of the sympathetic system and parasympathetic system may be substantially equal (i.e., neither is dominant).

By "bias", is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. As such, by "vagal bias", is meant that that the particular biased component of the autonomic nervous system that has a higher activity level than the other component is the vagus nerve or a portion of the autonomic nervous system associated with the vagus nerve. Vagal bias may be characterized by one or more of vagal dominance, vagal hypersensitivity and/or sympathetic insufficiency. The net result of the subject methods to treat a condition may be higher or greater sympathetic activity relative to parasympathetic activity in at least the area of the targeted autonomic system (i.e., that portion in need of modulation), or substantially equal activity levels of sympathetic activity and parasympathetic activity.

As noted above, in certain embodiments activity in at least a portion of the autonomic nervous system is increased. For example, any portion of the sympathetic system, e.g., one or more nerve fibers, may be pharmacologically and/or electrically stimulated to increase sympathetic activity to provide the desired ratio of parasympathetic/sympathetic activity. In other words, activity in at least a portion of the sympathetic nervous system may be increased pharmacologically and/or electrically such that at least a portion of the sympathetic nervous system may be "up-regulated".

In certain embodiments, increasing activity in, or up-regulating, at least a part of the sympathetic system may be desired in instances where, prior to the application of autonomic nervous system-modulating electrical energy and/or the administration of an effective amount of at least one pharmacological agent, parasympathetic activity is higher than desired, e.g., higher than sympathetic activity (e.g., there exists a relative parasympathetic bias) and as such the subject methods may be employed to increase sympathetic activity to a level above or rather to a level that is greater than parasympathetic activity or may be employed to modulate the differential between the parasympathetic-sympathetic systems such that the result of increasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase sympathetic activity above that of parasympathetic activity and/or may be employed to modulate (increase or decrease) the differential between the two systems, but in certain embodiments may be employed to decrease the parasympathetic activity/sympathetic activity ratio.

In certain embodiments, a parasympathetic bias may be the normal state, but the ratio of the two systems may be abnormal or otherwise contributing to a condition. Increasing sympathetic bias may also be desired in instances where, prior to the application of autonomic nervous system-modulating the administration of an effective amount of at least one pharmacological agent and/or electrical energy, sympathetic activity is higher than the parasympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low).

For example, such instances may occur where a subject has normal or above normal sympathetic function, but also has elevated parasympathetic function. Other instances may include below normal sympathetic function, but normal or elevated parasympathetic function, etc. It may also be desirable to increase sympathetic function in instances where the respective activities of the two system are analogous or approximately equal, including equal, prior to increasing activity in the sympathetic system, but the level of one or both is abnormally high or abnormally low. The above-described examples of instances where increasing sympathetic activity may be desired is exemplary only and is in no way intended to limit the scope of the invention and other instances where increasing sympathetic activity may be desired will be apparent to those of skill in the art.

As noted above, in certain embodiments activity in at least a portion of the parasympathetic system may be inhibited to modulate at least a portion of the autonomic nervous system. For example, activity in any portion of the parasympathetic nervous system may be inhibited, e.g., to provide the desired ratio of parasympathetic/sympathetic activity, e.g., activity in one or more parasympathetic nerve fibers may be inhibited. By "inhibited" is meant to include disruption, down-regulating, dampening and partial and complete blockage of nerve impulses in a particular area of the autonomic nervous system.

Inhibiting or "down-regulating" activity in at least a part of the autonomic nervous system, e.g., in at least a portion of the parasympathetic system, may be desired in instances where, prior to the inhibition of activity in, e.g., at least one parasympathetic nerve fiber, the parasympathetic activity is higher than desired. For example, parasympathetic activity may be higher than the sympathetic activity (i.e., there exists a parasympathetic bias) or parasympathetic activity may be less than or approximately equal to, including equal, to sympathetic activity, and the subject methods may be employed to modulate the differential between the parasympathetic-sympathetic systems such that the net result of decreasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., increased or reduced in certain embodiments. Accordingly, the subject methods may be employed to decrease parasympathetic activity below that of sympathetic activity and/or may be employed to modulate (decrease or increase) the differential between the two systems, where in certain embodiments may be employed to decrease the ratio of parasympathetic activity to sympathetic activity.

For example, decreasing activity in at least a portion of the parasympathetic system may be employed where there is a normal or an abnormally low sympathetic function and/or abnormally high parasympathetic function. Such may also be desired in instances where, prior to decreasing parasympathetic function in, e.g., at least one parasympathetic nerve fiber, sympathetic activity is higher than the parasympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing parasympathetic activity may be desired is exemplary only and is in no way intended to limit the scope of the invention and other instances where decreasing parasympathetic activity to provide an increase in the parasympathetic activity/sympathetic activity ratio may be desired will be apparent to those of skill in the art.

One way of inhibiting activity in at least a portion of the autonomic nervous system is by the application of a nerve block. Application of a nerve block at least partially prevents nerve transmission across the location of the block. A nerve block can be administered to modulate autonomic function using all the methods and devices described herein including pharmacological and/or electrical means.

In some embodiments, a nerve block is applied to at least a portion of the vagus nerve and is called a "vagal block". Where a vagal block is applied, autonomic function in a portion of the autonomic nervous system associated with the vagus nerve can be modulated using the vagal block. In some embodiments, a nerve block is removable. In embodiments in which a nerve block is removable, removal of the nerve block restores normal or pre-existing nerve activity at the location of the block.

As the subject methods include modulating at least a portion of a subject's autonomic nervous system, the modulation may be systemic or regional (i.e., localized). In other words, the entire autonomic nervous system may be modulated (e.g., the entire sympathetic nervous system and/or parasympathetic nervous system may be modulated) or only a portion of the autonomic nervous system may be modulated (e.g., only a portion of the sympathetic nervous system and/or parasympathetic nervous system may be modulated). Localization may be with respect to a particular area, organ or even to a particular nerve fiber. For example, localization may be with respect to innervations of one or more organs.

As noted above, in certain embodiments activity in at least a portion of the autonomic nervous system may be increased and activity in at least a portion of the autonomic nervous system may be decreased. For example, in certain embodiments activity in at least a portion of the sympathetic system may be increased and activity in at least a portion of the parasympathetic system may be inhibited, e.g., to decrease the parasympathetic activity/sympathetic activity ratio. As described above, any portion of the parasympathetic and/or sympathetic nervous systems may be electrically and/or pharmacologically modulated to increase activity and activity in any portion of the sympathetic and/or parasympathetic nervous system may be inhibited to provide the desired ratio of parasympathetic activity to sympathetic activity. Such a protocol may be employed, e.g., in instances where sympathetic function is normal or abnormally low and/or parasympathetic function is normal or abnormally high where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the parasympathetic system may be higher than activity in the sympathetic system and the subject methods may be employed to increase the sympathetic activity to a level that is greater than the parasympathetic activity and/or may be employed to alter the differential or difference in activity levels of the two systems such as decreasing the difference in activity levels or increasing the difference in activity levels.

Increasing activity in at least a portion of the autonomic nervous system, e.g., increasing activity in at least a portion of the sympathetic system, and decreasing activity in at least a portion of the autonomic nervous system, e.g., decreasing activity in at least a portion of the parasympathetic system, may be performed simultaneously or sequentially such that at least a portion of the autonomic nervous system, e.g., at least a portion of the sympathetic system, may be pharmacologically and/or electrically modulated to increase activity therein prior or subsequent to inhibiting activity in at least a portion of the autonomic nervous system e.g., at least a portion of the parasympathetic nervous system, such as by electrical and/or pharmacological means.

Regardless of whether increasing activity in at least a portion of the autonomic nervous system, e.g., in at least a portion of the sympathetic system, and decreasing activity in at least a portion of the autonomic nervous system, e.g., in at least a portion of the parasympathetic system, is performed simultaneously or sequentially, the parameters for increasing activity in at least a portion of autonomic nervous system and decreasing activity in at least a portion of the autonomic nervous system may be analogous to that described above.

Modulation of the autonomic nervous system may be accomplished using any suitable method, including employing electrical, thermal, vibrational, magnetic, acoustic, baropressure, optical, or other sources of energy to modulate autonomic balance, where in representative embodiments modulation is achieved via pharmacological modulation and/or electrical energy modulation in a manner that is effective to treat a subject for a food allergy syndrome condition. Certain embodiments include pharmacologically or electrically modulating at least a portion of a subject's autonomic nervous system, e.g., that portion associated with the respiratory, digestive, integumentary or cardiovascular systems, e.g., that directly or indirectly modulates the autonomic activity of the respiratory, digestive, integumentary or cardiovascular systems, e.g., by decreasing parasympathetic activity and/or increasing sympathetic activity in at least a portion of the subject's autonomic nervous system. In certain embodiments, modulation may include increasing the sympathetic activity/parasympathetic activity ratio in at least a portion of the subject's autonomic nervous system. In certain embodiments, both electrical and pharmacological modulation may be employed.

Pharmacologic Modulation

As noted above, certain embodiments of the subject invention may include treating a subject for a food allergy syndrome condition by pharmacologically modulating at least a portion of the subject's autonomic nervous system. By "pharmacologically modulating at least a portion of a subject's autonomic nervous system" is meant altering or changing at least a portion of an autonomic nervous system by pharmacological means to provide a change, alteration or shift in at least one component or aspect of the autonomic nervous system. In embodiments in which pharmacological agent is administered, any suitable protocol may be used, where certain protocols include using an pharmacological agent administering device to deliver a suitable amount of pharmacological agent to a subject. Methods and corresponding devices and systems for applying at least one pharmacological agent to a subject and which may be adapted for use in the subject invention are described, e.g., in U.S. Pat. Nos. 7,363,076; 7,149,574, U.S. patent application Ser. Nos. 10/661,368; 10/748,976; 10/871,366; 10/846,486; 10/917,270; 10/962,190; 11/060,643 11/251,629; 11/238,108; 11/592,027; 60/654,139; and 60/702,776; the disclosures of which are herein incorporated by reference.

Any convenient pharmacological agent may be employed. Pro-sympathetic agents of interest include, but are not limited to: beta agonists, e.g., dobutamine, metaproterenol, terbutaline, ritodrine, albuterol; alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL); indirect agents that include norepinephrine, e.g., ephedrine, ampthetamines, phenylpropanolamines, cyclopentamines, tuaminoheptanes, naphazolines, tetrahydrozolines; epinephrine; norepinephrine; acetylcholine; sodium; calcium; angiotensin I; angiotensin II; angiotensin converting enzyme I ("ACE I"); angiotensin converting enzyme II ("ACE II"); aldosterone; potassium channel blockers and magnesium channel blockers, e.g., valproate (sodium valproate, valproic acid), lithium; cocaine; amphetamines; terbutaline; dopamine; doputamine; antidiuretic hormone ("ADH") (also known as vasopressin); oxytocin (including PITOCINE); THC cannabinoids; and combinations thereof.

Electrical Modulation

In certain embodiments, to accomplish the modulation of at least a portion of a subject's autonomic nervous system, electrical energy (electrical modulation) may be applied to at least a portion of a subject's autonomic nervous system, where such electrical energy may be excitatory or inhibitory and in certain embodiments may include both excitatory and inhibitory stimulation. By "electrically modulating at least a portion of a subject's autonomic nervous system" is meant altering or changing at least a portion of an autonomic nervous system by electrical means to provide a change, alteration or shift in at least one component or aspect of the autonomic nervous system. Embodiments of the subject methods may also, in addition to electrical energy, include administering at least one pharmacological agent (pharmacological modulation) to said subject to modulate at least a portion of a subject's autonomic nervous system.

Any suitable area may be targeted for electrical modulation. Areas that may be targeted include, but are not limited to, pre- and post-ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency, e.g., to increase or decrease the sensitivity of a synapse and include modulating presynaptic neurons. In certain embodiments, electrical energy is applied using any of the devices described below.

A number of different methods and corresponding devices and systems for applying electrical energy to a subject and which may be adapted for use in the subject invention are described, e.g., in U.S. Pat. Nos. 7,149,574; 7,711,430; and 7,363,076; as well as U.S. patent application Ser. No. 11/592,027; the disclosures of which are herein incorporated by reference.

In some instances where an electrical protocol is employed, the target condition is not a bronchoconstriction condition, such as asthma, e.g., as described in United States Patent Application 20120004701.

Paradoxical Modulation

In some instances, the methods include employing a paradoxical protocol in order to obtain the desired increase is sympathetic/parasympathetic activity ratio. In these embodiments, the sympathetic/parasympathetic activity ratio is decreased initially in a manner effective to cause the subject to mount a compensatory response effective to ultimately increase the sympathetic/parasympathetic activity ratio. In certain embodiments, the magnitude of decrease in the sympathetic/parasympathetic activity ratio is two-fold or greater, e.g., 5-fold or greater.

In practicing the subject methods, the sympathetic/parasympathetic activity ratio is decreased by applying an appropriate stimulus to the subject, where the stimulus is of a nature and magnitude sufficient to achieve the desired enhancement. In certain embodiments, the applied stimulus is one of short duration, where by short duration is meant that the applied stimulus lasts for less than about 1 week, e.g., less than about 3 days, e.g., less than about 1 day, e.g., less than about 12 hours, where the duration of the applied stimulus may be even shorter. Where the stimulus is a pharmacological stimulus, the duration refers to the period in which the pharmacological agent from an administered dosage is active. Where the stimulus is an electrical stimulus, the duration refers to the total of electrical applications received by a subject over a given period, analogous to a dose of a pharmacological agent.

Following decrease of the sympathetic/parasympathetic activity ratio via an applied stimulus, as described above, the stimulus is removed, e.g., by metabolization of the pharmacological agent or cessation of application of electrical energy, and the subject is permitted to mount a compensatory response. In this following period, no additional stimulus is administered to the subject. The duration of this period between stimulus application, which may be referred to as a "holiday" period, may vary, but in representative embodiments is 1 day or longer, such as 2 days or longer, including 5 days or longer, 10 days or longer, e.g., 15 days or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in certain embodiments the stimulus may be a pharmacological stimulus and/or an electrical stimulus. As such, in certain embodiments, the stimulus is a pharmacological stimulus. In other embodiments, the stimulus is an electrical stimulus. In yet other embodiments, the stimulus is a combination of pharmacological and electrical stimuli. Accordingly, in certain embodiments, the enhancing is by administering a pharmacological agent to the subject. In yet other embodiments, the enhancing is by electrical stimulation, e.g., by employing an implanted electrical energy application device.

Representative pharmacological agents that may find use in certain embodiments of the subject invention include both pro parasympathetic agents. Pro parasympathetic agents of interest include, but are not limited to: Beta Blockers, Aldosterone Antagonists; Angiotensin II Receptor Blockers; Angiotensin Converting Enzyme Inhibitors; Statins; Triglyceride Lowering Agents; Insulin Sensitizers; Insulin Secretagogues; Insulin Analogs; Alpha-glucosidase Inhibitors; SGLT2 Inhibitors; Immunomodulators, including agents that bind/react to CD4, gp39, B7, CD19, CD20, CD22, CD401, CD40, CD40L and CD23 antigens; Sympathomimetics; Cholinergics; Calcium Channel Blockers; Sodium Channel Blockers; Glucocorticoid Receptor Blockers; Peripheral Adrenergic Inhibitors; Blood Vessel Dilators; Central Adrenergic Agonists; Alpha-adrenergic Blockers; Combination Diuretics; Potassium-sparing Diuretics; Nitrate Pathway Modulators; Cyclic Nucleotide Monophosphodiesterase (PDE) Inhibitors; Vasopressin Inhibitors; Renin Inhibitors; Estrogen and Estrogen Analogues and Metabolites; Vesicular Monoamine Transport (VMAT) Inhibitors; Progesterone Inhibitors; Testosterone Inhibitors; Gonadotropin-releasing Hormone Inhibitors; Dipeptidyl Peptidase IV inhibitors; Anticoagulants; Thrombolytics.

Instead of, or in addition to, pharmacological protocols, electrical protocols may be employed in these paradoxical approaches. In such instances, an electrical protocol is employed to obtain the desired paradoxical decrease in sympathetic/parasympathetic activity ratio. As reviewed above, a number of different methods and corresponding devices and systems for applying electrical energy to a subject and which may be adapted for use in the subject invention are described, e.g., in U.S. Pat. Nos. 7,149,574; 7,711,430; and 7,363,076; as well as U.S. patent application Ser. No. 11/592,027; the disclosures of which are herein incorporated by reference.
Subjects The methods described herein may be employed with a variety of different types of subjects, i.e., animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

In some embodiments, the subject in which autonomic function is modulated has been diagnosed as having a parasympathetic bias mediated condition. In some instances, the methods may include diagnosing the subject as having a parasympathetic bias mediated condition. Diagnoses of such conditions may be made using any convenient protocol. In some instances, the subject is also one that has been determined to have an autonomic dysfunction. As used herein, the term "autonomic dysfunction" describes any disease or malfunction of the autonomic nervous system. A specific type of autonomic dysfunction of interest is parasympathetic bias. A specific type of parasympathetic bias of interest is vagal bias.

In certain embodiments modulation of at least a portion of a subject's autonomic nervous system is not performed unless one or more aspects of the autonomic nervous system are detected and indicate such modulation is necessary. One aspect that may indicate modulation is necessary is the existence of an autonomic dysfunction, such as parasympathetic bias, e.g. vagal bias.

In certain embodiments the subject has an autonomic dysfunction before diagnosis of an autonomic dysfunction (e.g. parasympathetic bias) occurs. Any suitable physical and/or chemical aspect or indicator of the autonomic nervous system may be employed by one or more of a doctor, nurse, medical professional or individual with appropriate expertise to diagnose an autonomic dysfunction.

An autonomic dysfunction in a subject may be tested for by detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system.

These and other methods and devices for detecting one or more aspects of the autonomic nervous system potentially indicating an autonomic dysfunction that may be employed by embodiments of the subject methods include those described in U.S. Pat. Nos. 7,899,527 and 6,490,480 and U.S. patent Ser. Nos. 10/861,566 and 12/727,560.
Specific Parasympathetic Bias Mediated Conditions and Methods of Treating the Same In further describing various aspects of the invention, specific parasympathetic bias medicated conditions and methods for their treatment are now described in greater detail below.
Food Allergy Syndrome Aspects of the invention include treating a food allergy syndrome condition in a subject. As used herein, the term "syndrome" refers to one or more symptoms that are characteristic of a specific disorder or disease. Thus, the phrase "food allergy syndrome" refers to one or more symptoms which are characteristic of or associated with a food allergy. As such, a food allergy syndrome condition is a condition associated with one or more symptoms characteristic of a food allergy. Accordingly, a food allergy syndrome condition is a condition that is related to reactions caused or exacerbated by a food allergy. Specific food allergy syndrome conditions that may be treated according to embodiments of the invention include, but are not limited to conditions having symptoms associated with the respiratory, digestive, integumentary, cardiovascular, and/or other body systems. In certain embodiments, food allergy syndrome conditions manifest as one or more symptoms, where such symptoms include, but are not limited to: bronchospasm, cough, rhinorrhea, angioedema, gastric hypermotility, urticaria, pruritis, eczema, fatigue, bradycardia, and/or hypotension. As the target condition of the methods described herein is a food allergy syndrome, the subject that is treated by methods of the invention is one that also has one or more food allergies with which the syndrome is associated.

The subject methods find use in a variety of applications in which it is desired to treat a subject for a food allergy syndrome condition, e.g., a food allergy syndrome condition that may be influenced by an abnormality in the subject's autonomic nervous system (e.g., a parasympathetic bias). In such methods, at least a portion of a subject's autonomic nervous system is modulated in a manner suitable to treat the subject for the condition, e.g., in a manner to decrease the parasympathetic activity/sympathetic activity ratio in certain embodiments, e.g., as applied to a portion of the respiratory, digestive, integumentary, cardiovascular, and/or other body systems.

The subject methods find use in the treatment of a variety of different food allergy syndrome conditions in which an abnormality in a subject's autonomic nervous system exists. By treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the food allergy syndrome condition being treated. As such, treatment also includes situations where the condition, or at least symptoms associated therewith, are completely inhibited, e.g. prevented from happening, or stopped, e.g. terminated, such that the subject no longer suffers from the food allergy syndrome condition, or at least the symptoms that characterize the condition.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different food allergy syndrome conditions. Such food allergy syndrome conditions include, but are not limited to: conditions associated with the respiratory system including bronchospasm, cough, and rhinorrhea; conditions associated with the digestive system including gastric hypermotility; conditions associated with the integumentary system including angioedema, urticaria, pruritus, atopic dermatitis, and eczema; conditions associated with the circulatory system including fatigue, bradycardia, and hypotension; and combinations thereof.

In some instances, methods of the invention may also result in treatment of symptoms of the food allergy for which the syndrome is associated. Such symptoms may vary, and may include: difficulty swallowing, hives, vomiting, shortness of breath, stomach cramps, runny nose, patches of scaly or itchy skin, nausea, nasal congestion, lightheadedness, rash, diarrhea, fainting, abdominal pain, and swelling of the eyelids, face, lips, tongue or other areas, low blood pressure, blocked airways, and combinations thereof.

Conditions Normally Treated with Steroids

Aspects of the invention include using an epinephrine active agent for treatment of conditions normally treated with steroids. By epinephrine active agent is meant epinephrine or a functional equivalent thereof, e.g., an analogue, derivative, etc. Epinephrine is a chiral molecule having the structure:

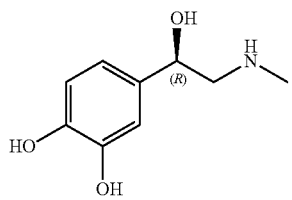

In some instances, the epinephrine active agent is epinephrine free base or a salt thereof, e.g., epinephrine hydrochloride, epinephrine bitartrate, etc.

Conditions normally treated with steroids which may be treated with an epinephrine active agent include, but are not limited to: ocular conditions, e.g., retinopathy, uveitis, a neovascularization disorder such as choroidal neovascularization, posterior segment neovascularization, or iris neovascularization, macular degeneration, macular edema, vein occlusion, ocular ischemic syndrome, orbital inflammatory diseases, surgically induced inflammation, thyroid-related orbital inflammatory disease, endophthalmitis, pain from a blind eye, hypotony, ocular vascular tumors, serous retinal detachment, chronic retinal detachment, idiopathic parafoveal telangectasia, iridocyclitis, papillitis, retinal vasculitis, keratitis, corneal transplant rejection, corneal melts, autoimmune diseases of the cornea and sclera, autoimmune-related eye and orbital diseases, chalazion, orbital pseudotumor, scleritis, and episcleritis; diseases of the skin or mucous membranes, which include but are not limited to the mouth, nasopharynx, respiratory tract, and gastrointestinal system, such as dermatitis, eczema, insect bites, lesions, ulcers, hemangiomas, vascular skin tumors, keloids, psoriasis, hypertrophic scars, traumatic scars, autoimmune skin disease, alopecia areata and other autoimmune disease that leads to hair loss, discoid lupus, esophageal strictures, and subglottic stenosis; musculoskeletal diseases, which include without limitation bursitis, synovitis, tendonitis, capsulitis, arthritis (including without limitation osteoarthritis, psoriatic arthritis, idiopathic arthritis, and rheumatoid arthritis), epicondylitis, back pain, and fasciitis; asthma, clinical inflammation, epicondylitis, endocrine disorders, lupus, rheumatic carditis, herpes zoster ophthalmicus, colitis, irritable bowel syndrome, ulcerative colitis, gastroenteritis, Crohn's disease, hemolytic anemia, leukemia, lymphoma, and rhinitis. In some embodiments, the methods of using epinephrine in treating conditions normally treated by steroids are not methods in which epinephrine is already known to treat the condition as of the filing date of this application.

Conditions Normally Treated with Epinephrine

Aspects of the invention include using a steroid active agent for treatment of conditions normally treated with epinephrine. By steroid active agent is meant a compound having four joined cycloalkane rings and having a suitable activity. Steroids of interest include, but are not limited to, glucocorticoids, where glucocorticoid of interest include, but are not limited to, dexamethasone, fluorometholone, medrysone, betamethasone, triamcinolone, triamcinolone acetonide, prednisone, prednisolone, hydrocortisone, rimexolone, prednicarbate, deflazacort, halomethasone, tixocortol, prednylidene, prednival, paramethasone, methylprednisone, meprednisone, mazipredone, isoflupredone, halopredone acetate, halcinonide, formocortal, flurandrenolide, fluprednisone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone, desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, aldlometasone, 21-acetoxypregnenolone, tralonide, diflorasone acetate, deacylcortivazol, RU-26988, deacyulcortivazol oxetanone, triamcinolone acetonide, prednisolone, prednisolone acetate, rimexolone, fluorormethalone, and fluorometholone acetate; hydrocortisoids; angiostatic steroids, such as hydrocortisone, tetrahydrocortisol-S, 11α-epihydrocotisol, cortexolone, 17α-hydroxyprogesterone, corticosterone, desoxycorticosterone, testosterone, estrone, dexamethasone, triamcinolone, and 6α-fluoro- 17,21-dihydroxy-16β-methyl-pregna-4,9,(11)-diene-3,20-dione, anecortave acetate; triamcinolones ((11β,16α)-9-fluoro-11,17,18,21-dihydroxy-pregna-1,4-diene-3,20-dione) or one of its derivatives such as, but not limited to, triamcinolone diacetate (10,16α)-16,21bis(acetyloxy)-9-fluoro-11,17-dihydroxypregna-1,4-diene-3-,20-dione); triamcinolone hexacetonide ((11β,16α)-21-(3,3-dimethyl-1-oxobutoxy)-9-fluoro-11-hydroxy-di-hydroxy-16,17-[1-methyldethylidenebis(oxy)]-pregna-1,4-diene-3,20-dione), or triamcinolone betonide ((11β,16α)-21-[3-benzoylamino-2-methyl-1-oxypropoxy]-9-fluoro-1-1-hydroxy-16,17-[1-methyldethylidenebis(oxy)]-pregna-1,4-diene-3,20-dione)-, triamcinolone acetonide ((11β,16α)-9-fluoro-11,21-dihydroxy-16,17-[1-methyld-ethylidenebis(oxy)]-pregna-1,4-diene-3,20-dione)).

Conditions normally treated with epinephrine which may be treated with an steroid active agent include, but are not limited to: disorders which are mediated by an alpha- or beta-receptor, such as blood pressures, vascular system conditions, the heart conditions; neurological disorders such as schizophrenia, Parkinson's disease and attention-deficit hyperactivity disorder; cardiac disorders, such as hypotension, forward failure, backward failure and congestive heart failure; vascular disorders, such as shock, hypotension, hemorrhage, and disorders associated with anesthesia; respiratory disorders, such as nasal congestion, oral and nasal inflammation and swelling (such as caused by cold or flu), chronic obstructive pulmonary disease, asthma, emphysema, and bronchospasm; gastrointestinal disorders, such as colic and Crohn's disease; anaphylaxis; interstitial cystitis; overactive bladder syndrome; premature labor; myasthenia gravis; glaucoma; dilation of pupils; and weight reduction. The term "anaphylaxis," as that term is used herein, refers to a broad class of immediate-type hypersensitivity and anaphylactic conditions well known to those skilled in the art including, but not limited to, anaphylactoid reactions, anaphylactic shock, idiopathic anaphylaxis, allergen induced anaphylaxis, exercise induced anaphylaxis, exercise-induced food-dependent anaphylaxis, active anaphylaxis, aggregate anaphylaxis, antiserum anaphylaxis, generalized anaphylaxis, inverse anaphylaxis, local anaphylaxis, passive anaphylaxis, reverse anaphylaxis, and systemic anaphylaxis. An "episode" of anaphylaxis, as that term is used herein, refers to a continuous manifestation of anaphylaxis in a patient. In some embodiments, the methods of using a steroid active agent in treating conditions normally treated by epinephrine are not methods in which a steroid is already known to treat the condition as of the filing date of this application.

Diagnosis and/or Prevention of Anaphylaxis

Aspects of the invention include methods of diagnosing and/or preventing anaphylaxis in a subject. The term "anaphylaxis" refers to an allergic condition that is rapid in onset and may be characterized by a number of symptoms, including itchy rash, throat swelling, and low blood pressure. The anaphylactic condition may result from a number of different causes, such as foods, medications, insect bites or stings, etc.

In some instances, autonomic function may be monitored in a subject, where occurrence of autonomic dysfunction (e.g., vagal bias) may be used to predict that a patient will have or is having an anaphylactic attack. The monitoring may be continuous and "real-time" in some instances, such that a subject is continuously monitored for the occurrence of autonomic dysfunction. Autonomic function (and therefore dysfunction thereof, e.g., vagal bias) may be monitored using any convenient protocol. An autonomic dysfunction in a subject may be tested for by detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system. These and other methods and devices for detecting one or more aspects of the autonomic nervous system potentially indicating an autonomic dysfunction that may be employed by embodiments of the subject methods include those described in U.S. Pat. Nos. 7,899,527 and 6,490,480 and U.S. patent Ser. Nos. 10/861,566 and 12/727,560. Employing autonomic function as an indicator that a subject is or will suffer from an anaphylactic attack may be used to predict the presence or occurrence of such an attack before other symptoms, e.g., as described above, may occur.

In some instances, these methods further include treating the subject for the anaphylactic attack prior to the occurrence of other symptoms, such as itchy rash, throat swelling, and low blood pressure. For example, where one has a subject that may be in danger of suffering from an anaphylactic attack, the subject can be monitored for autonomic dysfunction. For instance, continuous heart rate monitoring (proxy for vagal bias) may be employed for a subject who may be receiving oral immunotherapy (OIT) as a potential heralding sign of adverse immunologic reactions. If autonomic dysfunction is at least predicted to present, e.g., through diagnosis such as described above, interventional therapy for the anaphylactic attack, e.g., administration of epinephrine, may be employed to at least reduce the severity of one or more other symptoms of the attack (such as described above), if not prevent the occurrence of these one or more other symptoms of the attack.

In some instances, a closed-loop system or device may be employed. For example, a body associated device, e.g., an implanted or topical device, may be employed in such instances, where the device is configured to receive autonomic function data and, upon detection of autonomic dysfunction, administer an appropriate therapy, e.g., epinephrine, to the subject. The device may also be configured to obtain the autonomic function data. The device may be configured for long term association with the body of a subject, and may include additional components as desired, e.g., processors, power sources, etc.

Determining Treatment Protocol

Methods according to certain embodiments include determining a treatment protocol for a subject having a parasympathetic bias mediated condition, e.g., a predicted adverse response to a stimulus (such as therapeutic agent administration, nutritional ingestion, etc.). A "treatment protocol" for a subject having a target condition is a course of one or more actions which are taken to alleviate the condition or symptoms of the condition in the subject. The course of one or more actions which are taken to alleviate the condition or symptoms of the condition may include not taking action or not taking immediate action to treat the condition.

A treatment protocol for a subject having a target condition may include assessing whether the subject has an autonomic dysfunction (e.g., vagal bias). Such a determination also may include assessing the degree of autonomic function in a subject. The assessment of whether the subject has an autonomic dysfunction or the degree of autonomic dysfunction may be conducted using any appropriate methods including any of the methods described herein including detecting one or more aspects of the autonomic nervous system, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system potentially indicating an autonomic dysfunction including those described in U.S. Pat. Nos. 7,899,527 and 6,490,480 and U.S. patent application Ser. Nos. 10/861,566 and 12/727, 560; the disclosures of which are herein incorporated by reference.

After an assessment of whether the subject has an autonomic dysfunction is conducted, a determination of a treatment protocol for the subject for the target condition based on whether the subject has an autonomic dysfunction is made. The treatment protocol may include modulating autonomic function by modulating at least one portion of the subject's autonomic nervous system. As described above, modulating autonomic function may include treating the subject using any method or device, or a combination of the methods and/or devices, described or incorporated by reference herein. Such methods and devices specifically include those related to treatment using an electrical or pharmacological means. The determination in such instances may also include, or alternatively include, a recommendation to avoid circumstances that enhance parasympathetic bias, e.g., vagal bias, in the subject. The determination may also include, in some instances, a prescription for other treatment modalities, e.g., oral immunotherapy, in the subject.

The treatment protocol may also include specifically excluding autonomic function modulation if the subject does not have an autonomic dysfunction (e.g., vagal bias) or if the determining professional(s) determine modulation is unnecessary. In specifically excluding autonomic function modulation, a determination may be made to not perform autonomic function modulation of the subject if the subject does not have an autonomic dysfunction. Such a determination may include a determination that oral immunotherapy is sufficient to treat the food allergy.

The assessment and determination steps, e.g., as described above, may be conducted by one or more of a doctor, nurse, medical professional or individual with appropriate expertise. The assessing professional(s) may be the same as or different from the determining professional(s), e.g., as desired.

In certain embodiments, a computational system configured to perform the determination based on appropriate input is employed. Such as system may be configured to receive one or more data inputs regarding the subject and, based on such inputs, output to a user a treatment protocol, e.g., as described above.

An example of such an embodiment is where a potential adverse reaction to a given stimulus may occur if the subject has a parasympathetic, e.g., vagal, bias. For example, certain therapeutic agents have known high incidences of anaphylaxis, anaphylactoid reactions, or allergic reactions. Examples of such agents include, but are not limited to: β-lactam antibiotics (e.g., penicillin), aspirin, NSAIDs, chemotherapeutic agents, vaccines, protamine and herbal preparations. Prior to administration of such agents, the subject may be screened for the presence of parasympathetic, e.g., vagal, bias. If the subject is found to have such a bias, a suitable treatment protocol may be determined, e.g., to not administer the therapeutic agent, to administer a different agent with a reduced risk of the adverse effect, or to modulate the autonomic nervous system of the subject, e.g., as described above, to remove the bias prior to administration of the agent. For example, HRV may be employed in some instances as a measure of parasympathetic bias. In subjects with normal HRV, a determination may be made that therapeutic agents may be employed at normal or even higher dosages. In subjects determined to have low HRV (and therefore parasympathetic bias) a determination may be made to monitor the patient for side affects following administration of a therapeutic agent, or administration of lower dosages of such agents, or administration of other therapeutic agents not associated with side effects, e.g., as described further above.

Devices

A number of different devices and systems may be employed in accordance with the subject invention. Devices and systems which may be adapted for use in the subject invention include devices and systems for applying at least one pharmacological agent to a subject and devices and systems for applying electrical energy to a subject.

Devices and Systems for Applying Pharmacological Agent(S)

Different devices and systems for applying one or more pharmacological agents to a subject which may be adapted for use in the subject invention include embodiments configured to deliver pharmacological agent(s) using any of the methods described above. A device for applying one or more pharmacological agents to modulate autonomic function is a "pharmacological modulator".

Embodiments may include an implantable or external pharmacological delivery device such as, but not limited to, pumps, epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

In some embodiments, the device for applying one or more pharmacological agents includes a sensor for detecting a food allergy syndrome, condition, symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying at least one pharmacological agent according to the methods described above are made up of one or more of the devices or components listed or incorporated by reference herein.

Devices and systems for applying at least one pharmacological agent to a subject and which may be adapted for use in the subject invention are described, e.g., in U.S. Pat. Nos. 7,363,076; 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; 4,585,452; U.S. patent application Ser. Nos. 10/748,897; 10/748,976; 10/871,366; 10/846,486 10/917,270; 10/962,190; 11/060,643 11/251,629; 11/238,108; 11/592,027; 60/654,139; 60/702,776; and elsewhere, the disclosures of which are herein incorporated by reference.

Devices and Systems for Applying Electrical Energy

Devices and systems for applying electrical energy to a subject which may be adapted for use in the subject invention include embodiments configured to deliver electrical energy using any of the methods described above. In accordance with the subject methods to apply electrical energy to a subject, once operatively positioned, the electric energy applying device is activated to provide an electrical signal to the targeted area in a manner effective to practice the subject methods.

A device for applying electrical energy to modulate autonomic function is an "electrical modulator". Electrical modulators may be positioned directly on a targeted area and may be implantable within the body of the subject or be wholly or partially external to the subject's body. An electrical energy applying device or system typically includes a stimulator such as one or more electrodes, a controller or programmer and one or more connectors for connecting the stimulating device to the controller.

The one or more electrodes employed in the subject invention are controllable to provide output signals that may be varied in voltage, frequency, pulse width, current and intensity. The energy source for the electrical output may be provided by a battery or generator that is operatively connected to the electrode(s). The energy source may be positioned in any suitable location such as adjacent to the electrode(s), or a remote site in or on the subject's body or away from the subject's body in a remote location and the electrode may then be connected to the remotely positioned energy source using wires. A controller or programmer may also be coupled with an electric energy applying device. The programmer is typically one or more microprocessors under the control of a suitable software program.

In some embodiments, the device for applying electrical energy includes a sensor for detecting a food allergy syndrome condition symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying electrical energy according to the methods described above are made up of one or more of the devices or components listed or incorporated by reference herein.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect.

A number of different devices and systems for applying electrical energy to a subject and which may be adapted for use in the subject invention are described, e.g., in U.S. Pat. Nos. 7,149,574; 7,711,430; 7,363,076; U.S. patent application Ser. Nos. 10/661,368; 10/748,976; 10/871,366; 10/846,486 10/917,270; 10/962,190; 11/060,643 11/251,629; 11/238,108; 11/592,027; 60/654,139; and 60/702,776; and elsewhere, the disclosures of which are herein incorporated by reference.

The following examples are offered by way of illustration and not by way of limitation.

EXPERIMENTAL

We performed extensive autonomic testing on a 5-year-old subject with a history of virally-triggered asthma and severe tree nut allergy. The subject's heart rate was measured during deep breathing. During inhalation, activation of lung stretch receptors normally suppresses vagal activity, promoting tachycardia. The subject's heart rate during inhalation was 104 beats per minute, which is normal for a 5-year-old. During exhalation, unloading of lung stretch receptors reverses vagal suppression, typically reducing heart rate by 20 to 30 beats per minute (bpm). The subject's heart rate declined to 54 bpm, suggesting sympathetic underactivity. Heart rate response to $CO_2$ retention and release did not alter heart rate variability, suggesting central autonomic dysfunction, possibly at the brain stem level. Large fiber autonomic neuropathy was ruled out through additional testing. Skin sympathetic response (SSR) tests were performed limb-to-limb to localize the autonomic dysfunction. Delayed sympathetic function was observed only between the upper limbs, suggesting a possible defect somewhere along the cervico-thoracic sympathetic arc.

The findings appear consistent with the subject's history of asthma (characterized by expiratory wheeze and bronchospastic cough) and food allergy syndrome (anaphylaxis, angioedema, gastrointestinal cramping, hypotension, and bronchospasm). In the case of asthma, an allergic response to a viral antigen (characterized by degranulation, release of substance P, and activation of other cascading pathways) activates the autonomic afferent fibers, which are biased towards vagal dominance in this subject. During exhalation, insufficient sympathetic counter-response to vagal resurgence (associated with unloading of lung stretch receptors) results in expiratory wheeze (bronchoconstriction) and asthmatic cough (bronchospasm). In the case of food allergy syndrome, an allergic response to tree nut antigen (characterized by degranulation, release of vasoactive intestinal peptide, and activation of other pathways) triggers autonomic afferents.

Given the subject's underlying vagal bias, the subject exhibits symptoms consistent with vagal overload including angioedema, bronchoconstriction, hypotension, and gastrointestinal cramping. These are all hallmarks of anaphylaxis. The underlying autonomic dysfunction effectively turns a routine immunologic response to an antigen into a catastrophic, maladaptive response.

In the case of our 5-year-old subject, the origin of the subject's sympathetic under-responsiveness remains to be explored. Possible defect locations include end-organs, afferent fibers, brain stem, hypothalamus, spinal cord, and efferent fibers. Since the autonomic dysfunction appears regional, a genetic or cellular defect seems less likely, although secondary systemic consequences to the autonomic nervous system from chronic use of beta-agonists and steroids should be considered. There is a classic allergic reaction characterized by hyperreactivity of the respiratory and GI mucosa with type I hypersensitivity and provocative exposure leading to eosinophilia, plasma cells, and degranulated mast cells. The observations indicate that a vasomotor adjunct with an imbalance in ANS input results in the vasomotor, cardiovascular, and inflammatory anaphylaxis responses. The disease is characterized by the classic mismatch of parasympathetic over sympathetic drive of swelling, flushing, smooth muscle spasms, arterial spasm, and diarrhea.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of treating a subject, the method comprising:
   testing a subject that has not been previously diagnosed with a food allergy and has ingested a nutritional composition known to have a high incidence of allergic reaction to determine that the subject has parasympathetic bias and vagal bias by measuring one or more aspects of the subject's autonomic nervous system selected from the group consisting of: an amount of T helper cells, a conduction, a catecholamine level, heart rate variability, a hormone level, a chronotropic vasodilator response and an inotropic vasodilator response, to detect the parasympathetic bias and vagal bias; and
   modulating at least a portion of the tested subject's autonomic nervous system via an electrical protocol comprising applying an electrical stimulation to at least one nerve fiber of the subject via a device to increase the sympathetic/parasympathetic activity ratio in a manner effective to treat the subject for the food allergy.

2. The method according to claim 1, wherein the food allergy is an acute condition.

3. The method according to claim 1, wherein the modulating comprises decreasing parasympathetic activity.

4. The method according to claim 1, wherein the modulating comprises increasing sympathetic activity.

5. The method according to claim 1, wherein the vagal bias is characterized by one or more of vagal dominance, vagal hypersensitivity and sympathetic insufficiency.

6. The method according to claim 1, wherein the stimulating inhibits activity in at least one parasympathetic nerve fiber or inhibits nerve pulse transmission in the at least one parasympathetic nerve fiber.

7. The method according to claim 1, wherein the stimulating increases activity in at least one sympathetic nerve fiber.

8. The method according to claim 1, wherein the method comprises both decreasing parasympathetic activity and increasing sympathetic activity.

9. The method according to claim 8, wherein the method comprises both stimulating to inhibit activity or nerve pulse transmission in at least one parasympathetic nerve fiber and stimulating to increase activity in at least one sympathetic nerve fiber.

10. The method according to claim 1, wherein the increase in the sympathetic/parasympathetic activity ratio resulting from the modulation is quantified.

11. The method according to claim 1, wherein the subject has normal or above normal sympathetic function.

12. The method according to claim 1, wherein the subject has one or more undesirable symptoms selected from the group consisting of: difficulty swallowing, hives, vomiting, shortness of breath, stomach cramps, runny nose, patches of scaly or itchy skin, nausea, nasal congestion, lightheadedness, rash, diarrhea, fainting, abdominal pain, swelling, low blood pressure and blocked airway.

13. The method according to claim 1, wherein the one or more aspects of the autonomic nervous system comprises heart rate variability.

14. The method according to claim 13, wherein the testing comprises real-time monitoring of heart rate variability of the subject.

15. A method of treating a subject:
   testing a subject that has been previously diagnosed with a food allergy to determine that the subject has parasympathetic bias and vagal bias by measuring one or more aspects of the subject's autonomic nervous system selected from the group consisting of: an amount of T helper cells, a conduction, a catecholamine level, heart rate variability, a hormone level, a chronotropic vasodilator response and an inotropic vasodilator response, to detect the parasympathetic bias and vagal bias; and
   modulating at least a portion of the tested subject's autonomic nervous system via an electrical protocol comprising applying an electrical stimulation to at least one nerve fiber of the subject via a device to increase the sympathetic/parasympathetic activity ratio in a manner effective to treat the subject for the food allergy.

16. The method according to claim 15, wherein the subject has ingested a nutritional composition known to have a high incidence of allergic reaction prior to the testing.

17. The method according to claim 15, wherein the one or more aspects of the autonomic nervous system comprises heart rate variability.

18. The method according to claim 16, wherein the testing comprises real-time monitoring of heart rate variability of the subject.

19. The method according to claim 15, wherein the modulating comprises decreasing parasympathetic activity.

20. The method according to claim 15, wherein the modulating comprises increasing sympathetic activity.

21. The method according to claim 15, wherein the subject has normal or above normal sympathetic function.

* * * * *